(12) United States Patent
Tang et al.

(10) Patent No.: US 8,625,084 B2
(45) Date of Patent: Jan. 7, 2014

(54) DISTANCE DETECTING INDUCTION DEVICE

(75) Inventors: Qiaomei Tang, Shanghai (CN); Hong-Chang Huang, Shanghai (CN)

(73) Assignee: Shanghai Kohler Electronics, Ltd., Shanghai (CN)

( * ) Notice: Subject to any disclaimer, the term of this patent is extended or adjusted under 35 U.S.C. 154(b) by 160 days.

(21) Appl. No.: 13/061,109

(22) PCT Filed: Aug. 27, 2009
(Under 37 CFR 1.47)

(86) PCT No.: PCT/CN2009/073577
§ 371 (c)(1),
(2), (4) Date: Sep. 15, 2011

(87) PCT Pub. No.: WO2010/022666
PCT Pub. Date: Mar. 4, 2010

(65) Prior Publication Data
US 2012/0229797 A1    Sep. 13, 2012

(30) Foreign Application Priority Data
Aug. 28, 2008   (CN) .......................... 2008 1 0042139

(51) Int. Cl.
*G01J 3/00* (2006.01)
*G01J 1/42* (2006.01)
*G01N 21/31* (2006.01)

(52) U.S. Cl.
CPC .................................. *G01N 21/314* (2013.01)
USPC .............................. 356/51; 356/213; 356/218

(58) Field of Classification Search
CPC ................................. G01J 3/00; G01N 21/314
USPC ............................................ 356/51, 213, 218
See application file for complete search history.

(56) References Cited

U.S. PATENT DOCUMENTS

| 4,402,095 A * | 9/1983 | Pepper .............................. 4/623 |
| 4,833,318 A | 5/1989 | Yonekura et al. |
| 5,025,516 A * | 6/1991 | Wilson .............................. 4/623 |
| 6,710,346 B2 * | 3/2004 | Brewington et al. ....... 250/341.8 |
| 7,232,111 B2 * | 6/2007 | McDaniel et al. ......... 251/129.04 |

(Continued)

FOREIGN PATENT DOCUMENTS

| CN | 1573286 A | 2/2005 |
| CN | 101042298 A | 9/2007 |

(Continued)

OTHER PUBLICATIONS

English translation of International Search Report and Written Opinion for International Application No. PCT/CN2009/073577, mail date Nov. 26, 2009, 11 pages.

(Continued)

*Primary Examiner* — Michael P Stafira
(74) *Attorney, Agent, or Firm* — Foley & Lardner LLP (57) ABSTRACT

A distance detection induction device 100 comprises a housing 1, a condensing lens 2, a circuit board 3 having multiple electronic components, an infrared light emitting means 4, a light receiving means 5 for receiving and sensing the reflected infrared light. The housing 1 comprises a main body 10 and two round openings 11 and 12 on the top of the main body 10. The condensing lens 2 has an emitting lens 21 and a receiving lens 22 respectively located at the two round openings 11 and 12. The circuit board 3 bearing multiple electronic components for processing signal is mounted inside the main body 10. The infrared light emitting means 4 is to be infrared light-emitting diodes, emitting the infrared light to the emitting lens 21. The infrared light receiving means 5 is to be distance detecting sensing module, sensing the reflected light focused by the receiving lens 22. A connection part 23 having at least a bending part is set between the emitting lens 21 and the receiving lens 22. The distance detection induction device of the present invention has higher positioning precision and can enhance the induction performance of the whole device.

20 Claims, 7 Drawing Sheets

(56) References Cited

U.S. PATENT DOCUMENTS

2004/0001193 A1   1/2004  Takaoka
2005/0151101 A1*  7/2005  McDaniel et al. ....... 251/129.04
2007/0075280 A1*  4/2007  Nakano et al. ........... 250/559.38
2009/0056011 A1*  3/2009  Wolf et al. ........................ 4/623

FOREIGN PATENT DOCUMENTS

| CN | 101387515 A | 3/2009 |
| CN | 101387513 B | 6/2010 |
| CN | 101220883 B | 9/2010 |
| GB | 2352032 B | 7/2003 |

OTHER PUBLICATIONS

International Search Report for International Application No. PCT/CN2009/073577, mail date Nov. 26, 2009, 6 pages.

* cited by examiner

DISTANCE DETECTING INDUCTION DEVICE

CROSS-REFERENCE TO RELATED PATENT APPLICATIONS

This application is a U.S. National Phase Application claiming the benefit of and priority to International Application No. PCT/CN2009/073577, filed Aug. 27, 2009, which claims the benefit of and priority to Chinese Patent Application No. 200810042139.7, filed Aug. 28, 2008. The entire disclosures of International Application No. PCT/CN2009/073577 and Chinese Patent Application No. 200810042139.7 are incorporated herein by reference.

FIELD OF THE INVENTION

The present invention relates to an infrared induction device, particularly to a distance detection induction device applied in the automatic operation for sanitation and bathroom, such as automatic sensing faucet, automatic flush urinal etc.

BACKGROUND OF THE INVENTION

The infrared sensor has been widely used in the sanitary equipments, such as automatic sensing faucet, automatic flush urinal, flush facilities of the toilet, toilet seat having the hot water sprayer, hand dryer, toilet having the fan providing hot blast, etc.

Most of traditional infrared sensors adopt the active sensing method, i.e. the infrared emitter emits the infrared light with certain wavelength, and then the infrared receiver receives the infrared light after the reflection of the human body, further the infrared sensor judges the intensity of the reflected signals to realize the automatic sensing and judging. However, the infrared sensor could not complete the automatic sensing and judging if the target has low reflectivity to infrared light (for example, the black clothing, hair, etc.). There is only few infrared light could be received by the infrared receiver after the infrared light from the infrared emitter was reflected by such matter. The intensity of the reflected signals is not strong enough, so that the above infrared sensor fails to judge whether there is a target existing in the sensing area.

Figure 9:
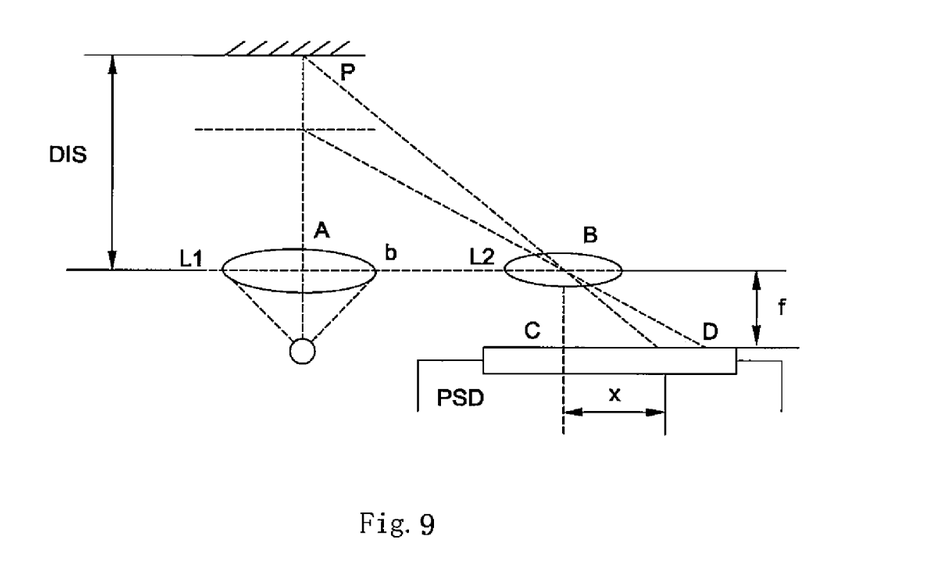
FIG. 9 is the principle figure of the distance detection induction device of the prior art.

To solve the above-mentioned problem of induction malfunction in the traditional infrared sensing sanitary ware, the Position Sensitive Detector (PSD) is introduced to the automatic operation for sanitation and bathroom. Shown as FIG. 9, the PSD sensor is a kind of photoelectric apparatus which is sensitive to the position of the incident light. When the incident light irradiates on the different position of the photosensitive surface of the PSD, the PSD will send out the different electrical signal. Using the triangulation principle, the PSD can accurately survey the distance to realize the auto-induction judgment. Shown as FIG. 9, the light from the light source irradiates on the surface of the detected target after focused by the lens L1. The reflected light is focused onto the one-dimensional PSD by the lens L2 and forms a luminous spot. If the distance between the center of the lens L1 and the center of the lens L2 is "b", the distance from the lens L2 to the surface of the PSD is "f", the distance between the luminous spot focused on the surface of the PSD and the center of the lens L2 is "x", the detected distance DIS can be expressed as: DIS=bf/x according to the principle of the similar triangles PAB and BCD. Therefore, so long as the value of the distance between the luminous spot focused on the surface of the PSD and the center of the lens L2 "x" is surveyed, the detected distance DIS can be determined.

When the distances of the detected target body fall into the pre-determined range, the distance detection induction device will control the sanitary fittings to work. Because the distance detection induction device achieves the purpose of the auto-induction by the way of judging the distance between the target and the distance detection induction device, not by the way of judging the intensity of the emitting signal, the problem of the induction malfunction caused by weak reflected signal in the traditional infrared sensing devices is solved.

However, it is necessary that the components of the distance detection induction device have higher positioning precision, therefore, so how to ensure the positioning precision of the Device need to be solved.

SUMMARY OF THE INVENTION

The object of the present invention is to provide a distance detection induction device having higher positioning precision.

The purpose of the present invention is realized by the following technical solutions: a distance detection induction device comprises a housing, a condensing lens, a circuit board, an infrared light emitting means, a light receiving means for receiving and sensing the light which is emitted by the infrared light emitting means and reflected by target, and a shielding cover. The housing comprises a main body and two round opening on the top of the main body. The condensing lens comprises an emitting lens and a receiving lens located at the opening of the housing. The circuit board bearing multiple electronic components for processing signal is mounted inside the main body of the housing. The infrared light emitting means is light-emitting diode fixed on said circuit board, and emits the infrared light to the emitting lens. The light receiving means is distance detecting sensing module fixed on said circuit board to sense the reflected light focused by the receiving lens. A connection part having at least a bending part is set between the emitting lens and the receiving lens.

Further, said connection part is bent twice as "z" shape.

Further, said lower parts of the condensing lens are made into the cylindrical structure.

Further, said condensing lens and said housing are combined together by injection molding.

Further, said distance detection induction device also comprises a sealing component mounted between the emitting lens and the infrared light emitting means or between the receiving lens and the light receiving means.

Further, the distance detection induction device also comprises a circuit wire disposing means fixed in the housing by screws.

Further, the distance detection induction device also comprises an indicator mounted on the circuit board and near the infrared light emitting means for demonstrating the normal or non-normal status of the distance detection induction device.

Further, said shielding cover is mounted around the infrared light emitting means and the light receiving means, keeping the infrared light emitting means and the light receiving means from the electromagnetic interference.

Further, said shielding cover comprises the first shielding cover and the second shielding cover, which are welded together, wherein the first shielding cover is fixed in the housing by screws and is touched with the circuit board for grounding, the second shielding cover is fixed to the housing by the clip structure, the infrared light emitting means and the light receiving means are mounted between the shielding cover and the circuit board.

Further, the housing is made of conducting material.

Compared with prior art, the components of the distance detection induction device of the present invention has higher positioning precision and can enhance induction performance of the overall device.

BRIEF DESCRIPTION OF THE DRAWINGS

FIG. 8 is the sectional drawing along A-A in FIG. 1a.

DETAILED DESCRIPTION OF THE INVENTION

The embodiments of the present invention will be clearly described referring the attached drawings, wherein the same figures are marked for the same structure parts or same function. It is understood that the attached drawings is just for the description of the embodiments of the present invention, not a limitation to the present invention. Besides, the attached drawings are not drawn as the pro rata.

Shown as FIG. 1 to FIG. 7, the distance detection induction device 100 of the present invention are mainly mounted on all kinds of the automatic sanitary equipments such as an urinal or toilet having automatic sensing device, a tap having automatic sensing device and so on.

The distance detection induction device 100 of the present invention mainly comprises a housing 1, a condensing lens 2 for focusing, a circuit board 3 bearing multiple electronic components, a infrared light emitting means 4 for emitting the infrared light, a light receiving means 5 for receiving and sensing the reflected infrared light and a shielding cover 6 having the function of electromagnetic shielding.

In the above device, the infrared light emitting means 4 and the light receiving means 5 are mounted on the same side of the circuit board 3. Shown as the embodiments of the present invention, the infrared light emitting means 4 and the light receiving means 5 are mounted onto the circuit board 3 by leg welding. The condensing lens 2 is fixed in the housing 1 and lens 2 comprises the emitting lens 21 which focuses and emits the infrared light and the receiving lens 22 which focuses the reflected infrared light onto the light receiving means 5.

For the distance detection induction device 100, the precise position between the infrared light emitting means 4 and the light receiving means 5 should be precisely set. The precise position among the infrared light emitting means 4, the light receiving means 5 and the condensing lens 2 should be precisely set too. Therefore, the distance detection induction device 100 of the present invention comprises an emitting positioning bracket 7 which fixes the infrared light emitting means 4, a receiving positioning bracket 8 which fixes the light receiving means 5. The emitting positioning bracket 7 and the receiving positioning bracket 8 hold the infrared light emitting means 4 and the light receiving means 5, and are coordinately positioned to the housing 1 to ensure the positioning precision of the infrared light emitting means 4 and the light receiving means 5.

Moreover, the shielding cover 6 is mounted on the periphery of the circuit board 3, and on the side that the infrared light emitting means 4 and the light receiving means 5 are mounted to prevent the infrared light emitting means 4 and the light receiving means 5 from the electromagnetic interference (EMI) of surroundings.

The housing 1 comprises a longitudinal long main body 10, the first round opening 11 and the second round opening 12 on the top of the main body 10. The condensing lens 2, the circuit board 3 bearing multiple electronic components, the infrared light emitting means 4, the light receiving means 5 and the shielding cover 6 are all set within the main body 10 of the housing 1. Correspondingly, the emitting lens 21 and the receiving lens 22 of the condensing lens 2 are respectively mounted in the first round opening 11 and the second round opening 12. The housing 1 is made of the insulating material such as ordinary plastic. Indeed, in another embodiment of the present invention, the housing 1 is made of the conducting material such as metal, conducting plastics to prevent from the electromagnetic interference effectively.

In the superior embodiments of the present invention, the emitting lens 21 and the receiving lens 22 of the condensing lens 2 are installed into the first round opening 11 and the second round opening 12 of the housing 1 by injection molding. Particularly, the installation of the condensing lens 2 and the housing 1 is made by injection molding twice. First, the condensing lens 2 is molded. Then, the molded condensing lens 2 is put into the mold of the housing 1 and is molded together with the housing 1. By injection molding, the problem of seal between the condensing lens 2 and the housing 1 is solved, and it also can ensure the relative positioning precision of the center of the condensing lens 2 and the housing 1. The lower parts of the emitting lens 21 and the receiving lens 22 are all made into the cylindrical structure to ensure the positioning precision during injection molding with the housing 1. Specially, the emitting lens 21 is connected with the receiving lens 22 by the connection part 23. In past design process, the emitting lens 21 and the receiving lens 22 are arranged alone. However, the relative position precision between the emitting lens 21 and the receiving lens 22, and the relative position precision between the condensing lens 2 and both of the infrared light emitting means 4 and the light receiving means 5 should be precisely set. It is not easy to control the position precision if the emitting lens 21 and the receiving lens 22 are established alone, and it is too hard to reach the requirements of precision. Thus, the emitting lens 21 and the receiving lens 22 are connected as a whole by a connection part 23 to ensure the position precision. Further, the connection part 23 has at least a bending part to prevent the emitted infrared light emitted by lens 21 from conducting into the receiving lens 22 along the connection part 23 directly. It avoids unnecessary reflection and refraction effect of internal light, and ensures the detecting precision of the distance detection induction device. As shown on FIG. 2 and FIG. 3, the connection part 23 is bended by several times as the "z" shape. Considered from the overall evaluation of cost and effect, in this structure it needs reflecting for two times for the emitted infrared light to conduct into the receiving lens 22 from the emitting lens 21. The optical path turns more complex, which can more effectively prevent the emitted infrared light emitted by lens 21 from conducting into the receiving lens 22 directly. Surely, the bending part can be increased or reduced according to the practical application situation. In another embodiment of the present invention, the condensing lens 2 and the housing 1 also can be mounted by assembly.

Multiple electronic components are integrated into the circuit board 3. The first hole 31 and the second hole 32 are placed just opposite to the emitting lens 21 and the receiving lens 22. The first hole 31 allows the emitting positioning bracket 7 passing through. The circuit board 3 processes the signal and transmits the processed data to the master-control unit. Thus, the sanitary fitting is controlled further (not shown in the figure).

Figure 1A:
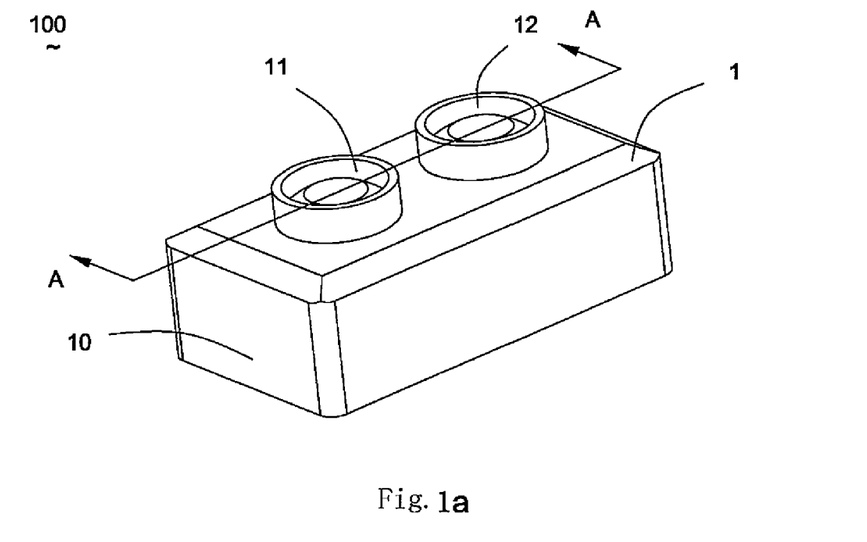
FIG. 1a is the three-dimensional view of the distance detection induction device of the present invention.
Figure 1B:
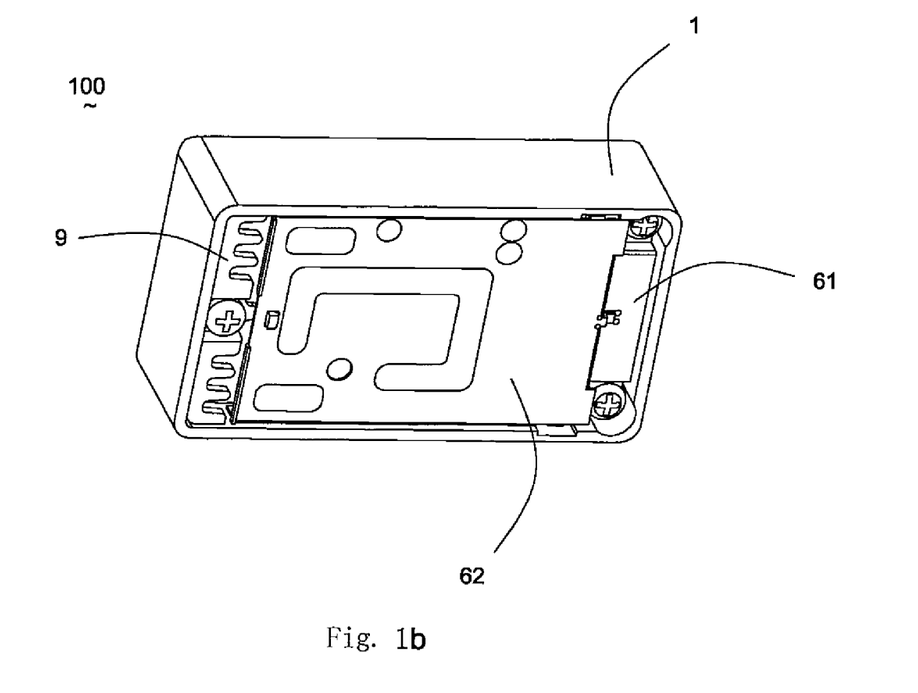
FIG. 1b is the three-dimensional view of the distance detection induction device of the present invention from other angle.
Figure 2:
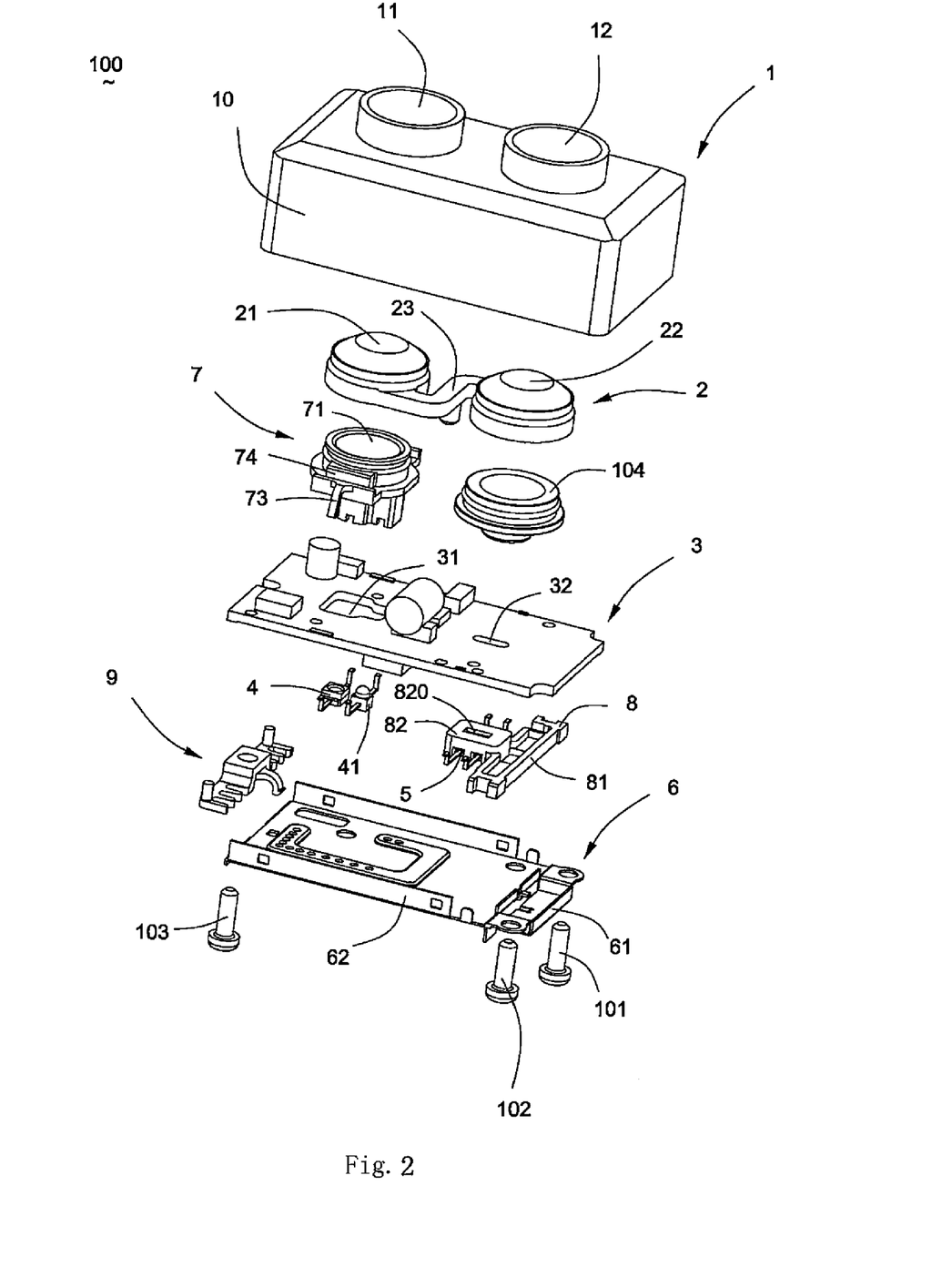
FIG. 2 is the exploded schematic drawing of the distance detection induction device of the present invention.
Figure 3:
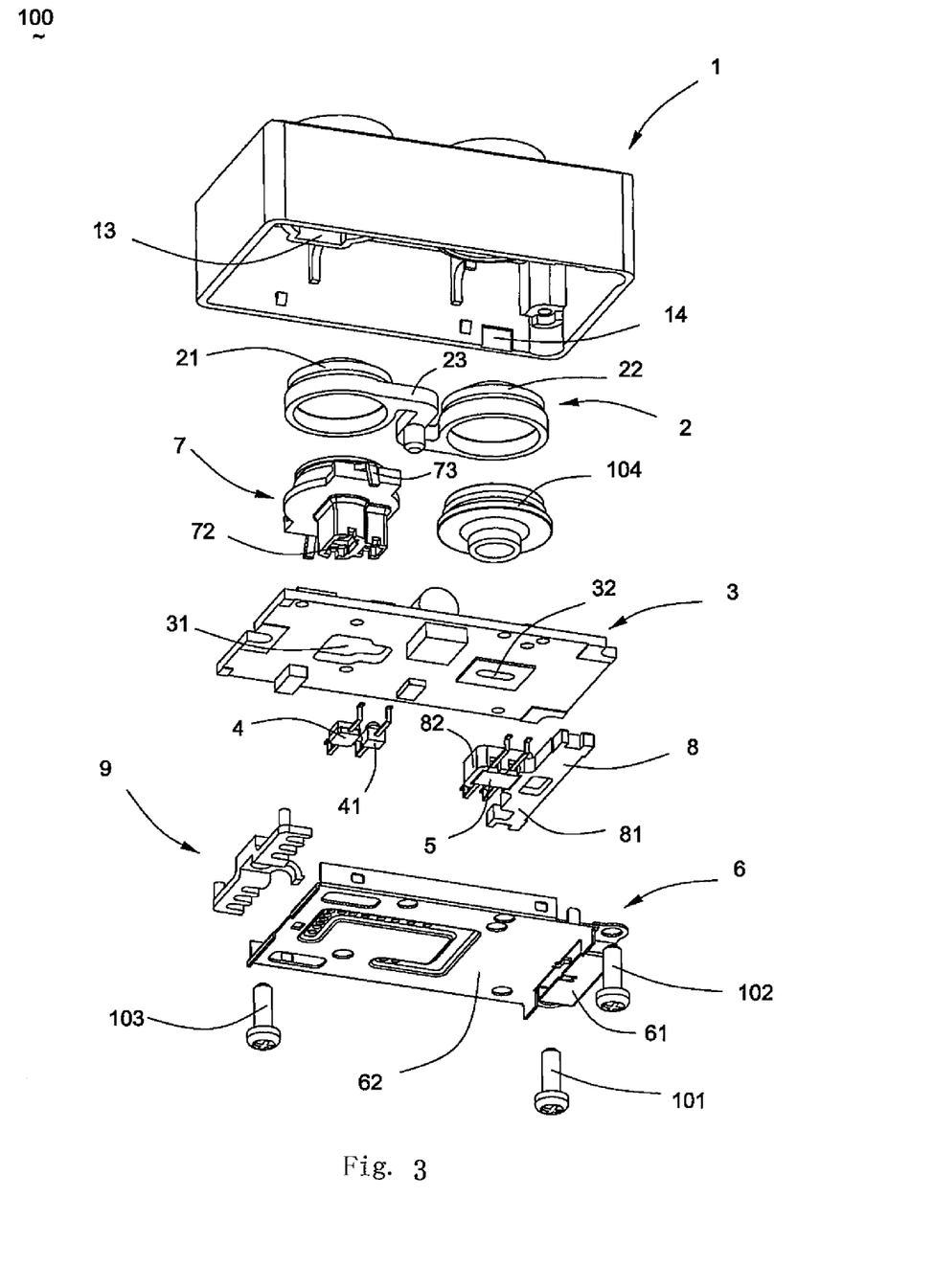
FIG. 3 is the exploded schematic drawing of the distance detection induction device of the present invention from other angle.
Figure 4A:
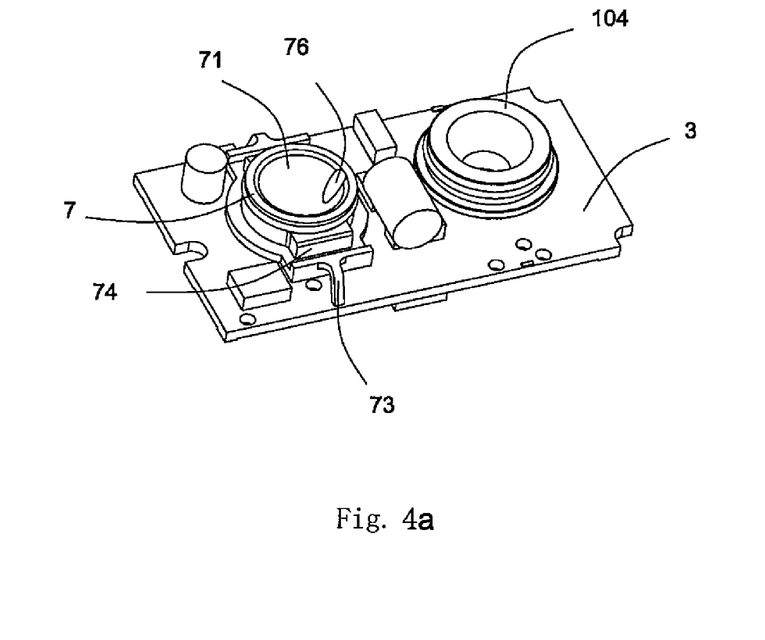
FIG. 4a is a part of the three-dimensional assembly chart of the distance detection induction device of the present invention.
Figure 4B:
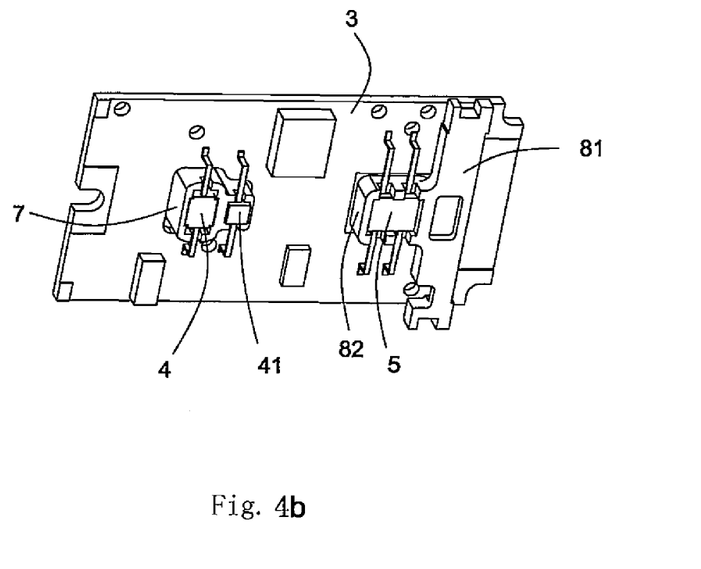
FIG. 4b is the schematic drawing of FIG. 4a from other angle.
Figure 4C:
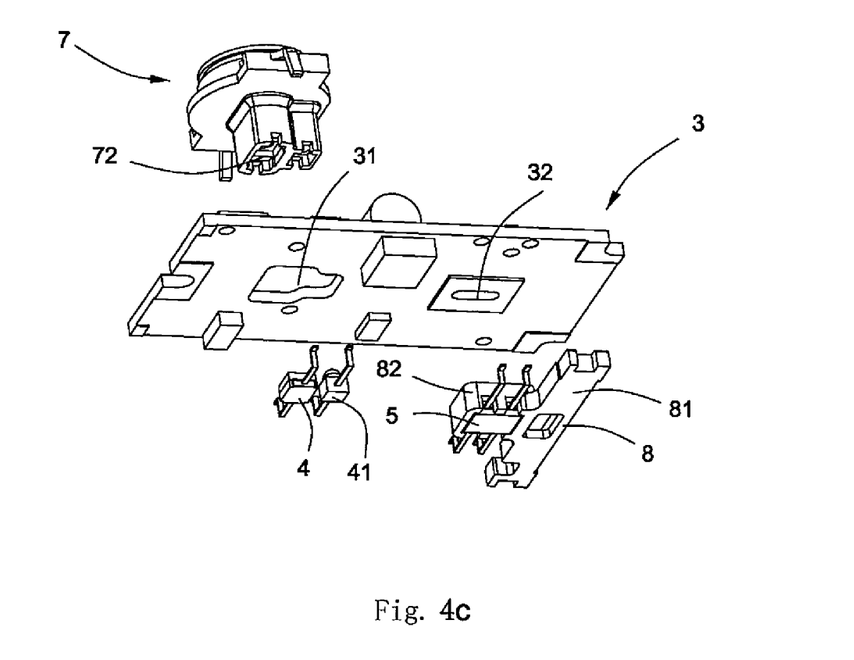
FIG. 4c is the exploded schematic drawing of the structure shown on FIG. 4b.
Figure 5:
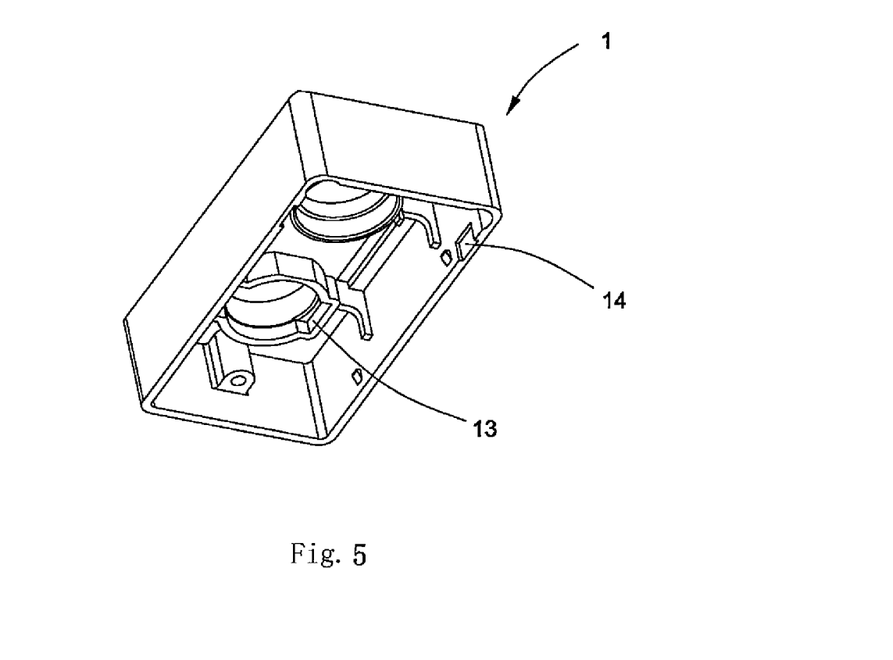
FIG. 5 is the view of the housing of the distance detection induction device of the present invention.

The infrared light emitting means 4 is infrared light-emitting diodes (IR LED) fixed on the circuit board 3, and located on the under side of the circuit board 3 (As shown as FIG. 2 and FIG. 3, The side of the circuit board 3 that faces the condensing lens 2 is the upside, and the opposite side is the under side of the circuit board 3). An indicator 41 is mounted on the under side of the circuit board 3 near the infrared light emitting means 4, and is used for demonstrating the normal or the non-normal working status of the distance detection induction device 100 such as the insufficiency of the battery capacity.

The light receiving means 5 is a distance detecting sensing module (PSD Sensing Module) fixed on the circuit board 3, and located on the under side of the circuit board 3.

The shielding cover 6 is fixed on the base of the housing 1 by the screws 101 and 102 to shield the infrared light emitting means 4 and the light receiving means 5. It includes the first shielding cover 61 and the second shielding cover 62. The first shielding cover 61 is fixed with the housing 1 and is touched with the ground line of the circuit board 3 by the screws 101 and 102 for grounding. The second shielding cover 62 is fixed with the housing 1 by the clip structure and is touched with the first shielding cover 61 by welding for grounding. It is better to set like the above-mentioned means, than to install a whole shielding cover, which will be not easy to be installed.

The emitting positioning bracket 7 is fixed with the housing 1. It includes a big round hole 71 at the top of the emitting positioning bracket 7 and coordinated with the emitting lens 21, and includes the holder 72 in the bottom of the emitting positioning bracket 7 to hold the infrared light emitting means 4. The diameter of the big round hole 71 is an approximate match to the emitting area of the emitting lens 21. The support stick 73 are set on two sides of the emitting positioning bracket 7 to press against the circuit board 3 closely, so that the circuit board 3 could provide enough bracket force to the emitting positioning bracket 7 correspondingly to avoid many problems, such as the emitting positioning bracket 7 dropping out from the housing 1 during the installation process. Specially, the emitting positioning bracket 7 also includes square protruding parts 74 at the two sides of the emitting positioning bracket 7. The square protruding parts 74 match with the positioning grooves 13 which are on the internal top of the housing 1, so that the emitting positioning bracket 7 and the housing 1 can be positioned. Surely, the square protruding parts 74 also can be set at other positions of the emitting positioning bracket 7 and can be other shapes such as a cylinder protruding stand. The holder 72 of the emitting positioning bracket 7 goes through the first hole 31 in the circuit board 3 from the upside of the circuit board 3, and takes in and positions the infrared light emitting means 4 on the under side of the circuit board 3. The weld legs of the infrared light emitting means 4 are bent after outstretching through the slots (not marked) on the two sides of the holder 72, and are welded on the circuit board 3. The emitting positioning bracket 7 is made of the insulating material. Of course, it also can be made of the conducting material. When the emitting positioning bracket 7 is made of the conducting material, it works as a shield to prevent from the electromagnetic interference.

Figure 6:
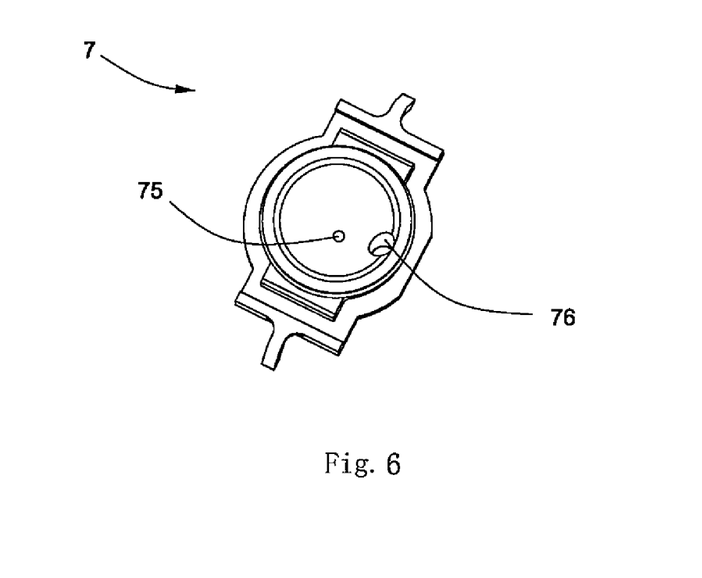
FIG. 6 is the view of the emitting positioning bracket of the distance detection induction device of the present invention.

Shown as FIG. 6, the emitting positioning bracket 7 also includes a small round hole 75 and an indicating hole 76. The small round hole 75 is near the holder 72 holding the infrared light emitting means 4, and the indicating hole 76 is to show the light emitted by indicator 41. Shown as FIG. 8, the small round hole 75 and the big round hole 71 form the cone-shaped channel of the infrared emission light, so the light is projected from the chip of the infrared light emitting means 4, passing through the small round hole 75 and the big round hole 71, and is projected out after focused by the emitting lens 21. Thus, the light is not projected to other regions of the housing 1 to avoid affecting the efficiency and introducing the light interference. No reflection and refraction of the interior light is projected to the light receiving means 5, and affects the detection effect. The chip of the infrared light emitting means 4 is so big that the emitting light has a big halo, which is a very disadvantageous factor to the light receiving means that needs precise signals and influences the detection result. In this embodiment of the present invention, the infrared light emitted out from the chip of the infrared light emitting means held in the holder 72 only passes through the small round hole 75 to project out. The light passes through the big round hole 71 and is focused by the emitting lens projecting out. The cross-section of the small round hole 75 is smaller than the light emitting area of the infrared light emitting means 4, and the unnecessary light is blocked. It effectively reduces the affection of the halo to the detection signal, and enhances the detection precision. In this case, the emitting positioning bracket 7 is working as the guide means of the emitted light.

Figure 7A:
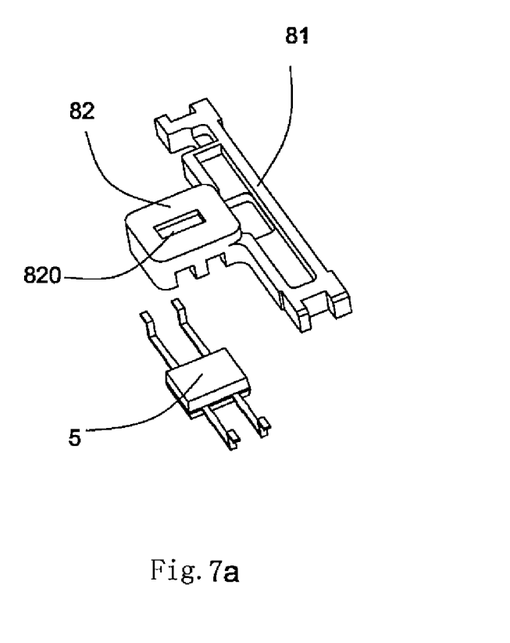
FIG. 7a is the exploded schematic drawing of the light receiving means and its positioning bracket of the distance detection induction device of the present invention.
Figure 7B:
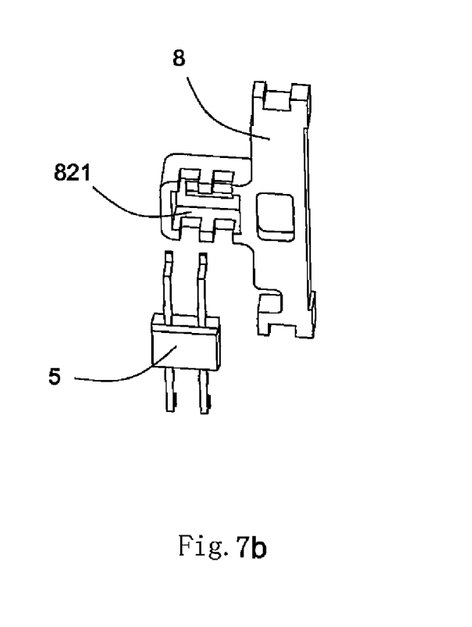
FIG. 7b is the view of FIG. 7a from other angle.

Shown as FIG. 7a and FIG. 7b, the receiving positioning bracket 8 comprises the transom 81 fixed onto the housing 1 and the holder 82 connected together with the transom 81. The holder 82 holds the light receiving means 5. The holder 82 has the holding space 821 holding the light receiving means 5. A rectangular aperture 820 is set on the top of the holder 82 aligning with the second hole 32 on the circuit board 3 to let the received light arrive at the receiving surface of the light receiving means 5. The holder 82 is formed by extending the middle part of the transom 81 horizontally, so the weld legs of the light receiving means 5 can extend out from the slots on the two sides of the holder 82 to conveniently make the welding. For effective positioning, the two free ends of the transom 81 are fitted with the positioning groove 14 on the two sidewalls of the main body 10 of the housing 1.

The distance detection induction device 100 of the present invention also includes a circuit wire disposing means 9. The circuit wire disposing means 9 can tidy up the wires (not shown in the figure) on the circuit board 3 effectively and fix them in the housing 1 by the screw 103.

The distance detection induction device 100 of the present invention also includes a sealing component 104 which mounted between the condensing lens 2 and the circuit board 3 for sealing. On one hand, the sealing component 104 can prevent the epoxy used for sealing from entering the light receiving means 5; for example, prevent the epoxy from entering the light receiving means 5 through the second hole 32. On the other hand, the sealing component 104 can prevent the interference light from entering the housing 1 or the light receiving means 5. In the present embodiment, the sealing component 104 is made of silicone rubber; of course, it also can be made of other sealing material. If permissible, similar seal structure can be used between the emitting lens 21 and the infrared light emitting means 4.

Figure 8:
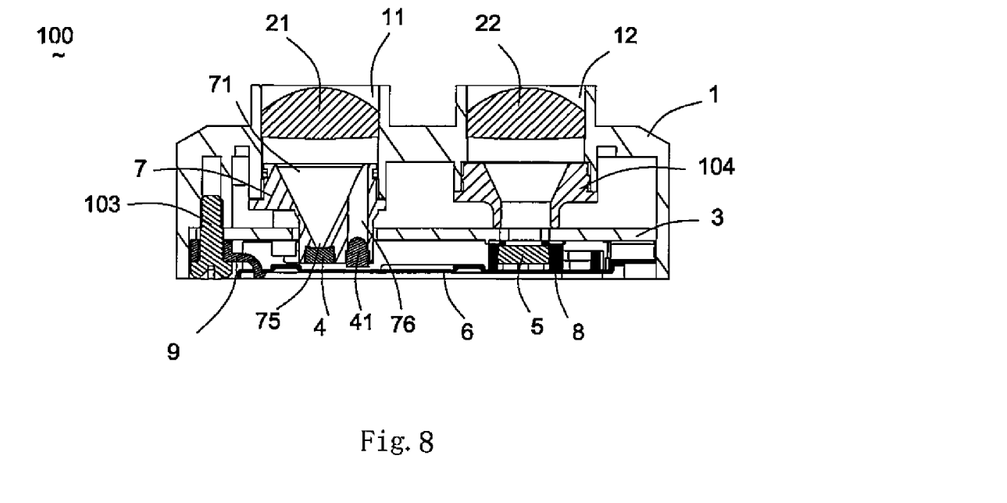

Shown as FIG. 8, the first hole 31 and the second hole 32 are set on the circuit board 3. The infrared light emitting means 4 projects the infrared emitting light to the emitting lens 21 through the first hole 31. The emitting lens 21 focuses the infrared emitting light to the target area. When human body or moving target goes into the target area, the infrared light is reflected. The receiving lens 22 receives and focuses the reflected infrared light onto the light receiving means 5 through the second hole 32. According to PSD triangulation principle, the light receiving means 5 surveys the distance of the target, then controls the sanitary fittings finally. Set like this, the infrared light emitting means 4 and the light receiving means 5 can be fixed on the under side of the circuit board 3 (The side of the circuit board 3 that faces the condensing lens 2 is the upside, and the opposite side is the under side of the circuit board 3). Because the focal distance of the condensing lens 2 is set with a determinate value, the thickness of the circuit board 3 can be part of the focal distance. Meanwhile, because other electronic components are set on the circuit board 3, it can make highly efficient use of the inner space of the housing 1 and the space on either of upside or underside of the circuit board 3 to install the infrared light emitting means 4 and 5 among these electronic components. Such arrangement reduces the height and the volume of the whole distance detection induction device 100.

Moreover, as the infrared light emitting means 4 and the light receiving means 5 are installed between the circuit board 3 and the shielding cover 6, which can block the exterior disturbance, and the external interference could be shielded effectively.

The infrared light emitting means 4 and the light receiving means 5 of the distance detection induction device 100 of the present invention are fixed by the positioning brackets 7 and 8 to ensure the positioning precision of the infrared light emitting means 4 and the light receiving means 5. The relative position of the infrared light emitting means 4 and the light receiving means 5 to the housing 1 can be ensured by fixing the positioning bracket 7 and 8 to the housing 1 coordinately. Since welding process starts after the infrared light emitting means 4 and the light receiving means 5 are fixed into the corresponding holders of the positioning bracket 7 and 8, so that the position precisions of the infrared light emitting means 4 and the light receiving means 5 are not influenced by the installment. Therefore, it solves the problem that the position precisions is influenced by installation, which exist in prior art. Thus, it effectively solves the problems that the distance detection induction device 100 does not work well or even doses not work caused by the bad installation precision when the infrared light emitting means 4 and the light receiving means 5 are installed to the circuit board 3.

Moreover, the production cost of the distance detection induction device 100 of the present invention is low, in favor of the popularization and application.

Although the present invention has been described and illustrated in detail, it is clearly understood that the same is by way of illustration and example only and is not to be taken by way of limitation, the spirit and scope of the present invention.

The invention claimed is:

1. A distance detection induction device comprising:
    a housing having a main body and two round openings in a top surface of the main body;
    a unitary condensing lens comprising an emitting lens, a receiving lens, and a connection part having at least one bend, wherein the emitting lens and the receiving lens are respectively located at the two round openings, and wherein the connection part fixedly connects the emitting lens to the receiving lens;
    a circuit board mounted inside the main body and bearing multi-electronic components, wherein the circuit board is used for signal processing;
    an infrared light emitting means including an infrared light-emitting diode mounted on the circuit board, wherein the infrared light emitting means is configured for emitting infrared light to the emitting lens;
    a light receiving means including a distance detecting sensing module mounted on the circuit board, wherein the light receiving means is configured for receiving and sensing the infrared light which is emitted by the infrared light emitting means, reflected by a target, and focused by the receiving lens; and
    a shielding cover.

2. The distance detection induction device according to claim 1, characterized in that said connection part is bent twice, as "z" shape, wherein the connection part is configured to prevent emitted infrared light from transmitting directly from the emitting lens to the receiving lens via the connection part.

3. The distance detection induction device according to claim 1, characterized in that the condensing lens includes a cylindrical structure projecting from a lower part thereof.

4. The distance detection induction device according to claim 1, characterized in that said condensing lens and said housing are installed together by injection molding.

5. The distance detection induction device according to claim 1, characterized in that said distance detection induction device also includes a sealing component mounted between said emitting lens and said infrared light emitting means or between said receiving lens and said light receiving means.

6. The distance detection induction device according to claim 1, characterized in that said distance detection induction device also includes a circuit wire disposing means fixed in said housing by screws.

7. The distance detection induction device according to claim 1, characterized in that said distance detection induction device also includes an indicator mounted on said circuit board and near said infrared light emitting means, wherein the indicator is configured to demonstrate a normal status or a non-normal status of the distance detection induction device.

8. The distance detection induction device according to claim 1, characterized in that said shielding cover is mounted around said infrared light emitting means and said light receiving means, keeping said infrared light emitting means and said light receiving means from the electromagnetic interference.

9. The distance detection induction device according to claim 8, characterized in that said shielding cover comprises a first shielding cover and a second shielding cover welded with said first shielding cover,
    wherein said first shielding cover is fixed in said housing by screws and is electrically grounded with said circuit board and wherein said second shielding cover is fixed to said housing by a clip structure, wherein said infrared light emitting means and said light receiving means are mounted between said shielding cover and said circuit board.

10. The distance detection induction device according to claim 1, characterized in that said housing is made of conducting material.

11. A precision positioning system for a distance detection induction device, the precision positioning system comprising:

an infrared light emitting means;

an emitting lens configured to focus and emit infrared light produced by the infrared light emitting means;

a receiving lens configured to receive and focus infrared light emitted by the emitting lens and reflected by a target;

a light receiving means including a distance detecting sensing module configured to receive the reflected and focused infrared light from the receiving lens, wherein the light receiving means is configured to produce an electrical signal in response to a position of the reflected and focused infrared light; and a connection part fixedly and directly connected with both the emitting lens and the receiving lens, the connection part positionally fixing the emitting lens and the receiving lens relative to each other;

wherein the emitting lens, the receiving lens, and the connection part are formed as a single unitary component from an optically transmissive material, wherein the connection part includes at least one bend configured to prevent emitted infrared light from transmitting from the emitting lens to the receiving lens via the connection part.

12. The precision positioning system of claim 11, further comprising:

a housing having a main body and two round openings in a top surface of the main body, wherein the emitting lens and the receiving lens are respectively aligned with the two round openings.

13. The precision positioning system of claim 12, further comprising:

an emitting positioning bracket fixed to the housing and disposed between the infrared light emitting means and the emitting lens, the emitting positioning bracket including a holder configured to hold the infrared light emitting means.

14. The precision positioning system of claim 13, wherein the emitting positioning bracket further includes:

a small hole for receiving the infrared light emitted by the infrared light emitting means, a large hole having a diameter approximately matching a diameter of the emitting lens, and a conical channel extending between the small hole and the large hole.

15. The precision positioning system of claim 13, wherein the emitting positioning bracket includes a positioning element configured to engage a corresponding positioning element disposed along an interior surface of the housing for positioning the emitting positioning bracket relative to the housing.

16. The precision positioning system of claim 13, further comprising:

a receiving positioning bracket fixed to the housing and including a holder configured to hold the light receiving means, wherein fixing the emitting positioning bracket and the receiving positioning bracket to the housing fixes a position of the infrared light emitting means and the infrared light receiving means relative to each other.

17. The precision positioning system of claim 12, further comprising:

a shielding cover configured to provide electromagnetic shielding for the infrared light emitting means and the light receiving means, wherein the infrared light emitting means and the light receiving means are disposed between the housing and the shielding cover.

18. The precision positioning system of claim 12, further comprising:

a circuit board mounted inside the main body and electrically connected with the infrared light emitting means and the light receiving means, wherein the circuit board is configured to receive and process the electrical signal produced by the light receiving means.

19. The precision positioning system of claim 18, wherein the infrared light emitting means and the light receiving means are positioned on a first side of the circuit board and the emitting lens and receiving lens are positioned on a second side of the circuit board;

wherein the circuit board includes a first hole and a second hole, both holes extending completely through the circuit board from the first side to the second side;

wherein the infrared light emitted by the infrared light emitting means passes through the first hole before reaching the emitting lens and wherein the reflected infrared light focused by the receiving lens passes through the second hole before reaching the light receiving means.

20. The precision positioning system of claim 18, further comprising:

a shielding cover configured to provide electromagnetic shielding for the infrared light emitting means and the light receiving means, wherein the infrared light emitting means and the light receiving means are disposed between the circuit board and the shielding cover.

* * * * *